(12) United States Patent
Jie et al.

(10) Patent No.: US 9,045,707 B2
(45) Date of Patent: Jun. 2, 2015

(54) ENVIRONMENTAL-FRIENDLY LIQUID FUEL AND PRODUCTION PROCESS THEREOF

(71) Applicant: Beijing Jinjiao Biomass chemical industry Co., Ltd, Beijing (CN)

(72) Inventors: Erwang Jie, Baotou (CN); Wei Zhang, Beijing (CN)

(73) Assignee: Beijing Jinjiao Biomass Chemical Industry Co., Ltd., Beijing (CN)

( * ) Notice: Subject to any disclaimer, the term of this patent is extended or adjusted under 35 U.S.C. 154(b) by 85 days.

(21) Appl. No.: 13/893,727

(22) Filed: May 14, 2013

(65) Prior Publication Data
US 2013/0305595 A1 Nov. 21, 2013

(30) Foreign Application Priority Data

May 17, 2012 (CN) .......................... 2012 1 0153661
Dec. 14, 2012 (CN) .......................... 2012 1 0543959

(51) Int. Cl.
| | |
|---|---|
| C10L 1/02 | (2006.01) |
| C07C 68/06 | (2006.01) |
| C10L 1/19 | (2006.01) |
| C07D 321/06 | (2006.01) |
| C07D 307/42 | (2006.01) |
| C10L 1/185 | (2006.01) |
| C10L 10/00 | (2006.01) |
| C10L 10/08 | (2006.01) |
| B01J 37/03 | (2006.01) |
| B01J 37/08 | (2006.01) |
| B01J 37/18 | (2006.01) |
| B01J 23/00 | (2006.01) |
| B01J 23/10 | (2006.01) |
| B01J 23/14 | (2006.01) |
| B01J 23/75 | (2006.01) |
| B01J 23/86 | (2006.01) |
| B01J 37/02 | (2006.01) |

(52) U.S. Cl.
CPC .............. *C10L 1/02* (2013.01); *C10L 2270/02* (2013.01); *C07C 68/06* (2013.01); *C10L 1/19* (2013.01); *C10L 2270/023* (2013.01); *C10L 2270/026* (2013.01); *C07C 2101/02* (2013.01); *C07D 321/06* (2013.01); *C07D 307/42* (2013.01); *C10L 1/1855* (2013.01); *C10L 10/00* (2013.01); *C10L 10/08* (2013.01); *B01J 37/031* (2013.01); *B01J 37/08* (2013.01); *B01J 37/18* (2013.01); *B01J 23/002* (2013.01); *B01J 23/10* (2013.01); *B01J 23/14* (2013.01); *B01J 23/75* (2013.01); *B01J 23/868* (2013.01); *B01J 37/0201* (2013.01); *B01J 2523/00* (2013.01)

(58) Field of Classification Search
CPC ....... C10L 10/00; C10L 10/08; C10L 1/1855; C10L 1/19; C10L 1/02; C07C 68/06; C07D 321/06; C07D 307/42; B01J 37/031; B01J 37/08; B01J 37/18; B01J 37/0201; B01J 23/002; B01J 23/10; B01J 23/14; B01J 23/75; B01J 23/868
USPC ............................................. 44/387; 558/277
See application file for complete search history.

(56) References Cited

U.S. PATENT DOCUMENTS

| | | | | |
|---|---|---|---|---|
| 4,380,455 | A | * | 4/1983 | Smith .............................. 44/387 |
| 5,430,170 | A | * | 7/1995 | Urano et al. ................... 558/277 |
| 5,498,743 | A | * | 3/1996 | Shih et al. ...................... 558/277 |
| 6,387,138 | B1 | * | 5/2002 | Murayama et al. ............. 44/387 |

FOREIGN PATENT DOCUMENTS

| | | | |
|---|---|---|---|
| CN | 1699326 | * | 11/2005 |
| CN | 1699328 | A | 11/2005 |
| CN | 101234965 | B | 8/2008 |
| CN | 102464587 | A | 5/2012 |
| CN | 102558106 | | 7/2012 |
| CN | 102676239 | | 9/2012 |

* cited by examiner

*Primary Examiner* — Cephia D Toomer
(74) *Attorney, Agent, or Firm* — Greer, Burns & Crain, Ltd.

(57) ABSTRACT

The present invention discloses a liquid fuel and production process thereof, the liquid fuel comprises dialkyl carbonates with the structural formula of

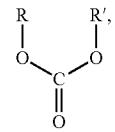

wherein R and R' are same or different, and R and R' are selected from the group consisting of C1-C8 linear chain alkyl, C3-C8 branched chain alkyl, C3-C8 naphthene base and alkyl containing furan ring. The process of the production of the liquid fuel comprises the steps of: performing a cycloaddition reaction between 2-methyl tetrahydrofuran produced by hydrogenation from furfural which is a biomass derivative and carbon dioxide to produce a cyclic carbonate (i.e. 1,4-pentanediol carbonate), then performing an ester exchange reaction between the cyclic carbonate and monohydric alcohol to produce the dialkyl carbonate. The liquid fuel produced is clean, safe and biodegradable, and the process provides a new way for industrial production of the dialkyl carbonate with remarkable economic and social benefit.

17 Claims, No Drawings

ENVIRONMENTAL-FRIENDLY LIQUID FUEL AND PRODUCTION PROCESS THEREOF

TECHNICAL FIELD

The present invention relates to a liquid fuel, in particular to an environmental-friendly liquid fuel and production method thereof.

BACKGROUND ART

The fuel can be classified into solid fuel, liquid fuel and gas fuel according to its form; it also can be classified into fossil fuel, biological fuel and nuclear fuel according to its type. Wherein, the liquid fuel includes crude oil and petroleum product, light diesel oil, heavy oil, gasoline, kerosene, coal tar, shale oil, synthetic oil, coal liquefaction oil, alcohol fuel and other liquid fuels.

Demand on energy is increasing with rapid development of world's economic, and energy problem has attracted more and more attentions from all aspects. Although fossil energy dominates at the present, coal, petroleum, natural gas and other mineral fuel resources are gradually exhausted due to serious exploration. From the nineties of the 20th century, under promotion of agricultural development, energy safety, climate change, environmental protection, etc., more and more countries actively participate in development of biological liquid fuel industry.

The biological liquid fuel is diverse in raw material resource, production technical route and product. Wherein, the biomass resource include lignocelluloses, starch, sugar, oil and grease of animal, plant and microorganism, etc., and the main product includes fuel ethanol, biological diesel oil, biological oil, catalytic hydrogenation biological diesel oil, biological methane, biological methanol, biological dimethyl ether, biological hydrogen, etc. The first generation of biological liquid fuel mainly includes fuel ethanol using starch and sugar from cane, corn, potato, etc. as raw material and biological diesel oil using grease as raw material. These products have long-term industrial application experience and comparatively mature technology. These products have good compatibility with the existing vehicle fuel and engine, and large-scale commercial production and application are realized. However, the energy crop which is adopted to develop the biological liquid fuel has remarkable problems of pushing up the costs of agricultural products and foods and threatening safety of grains, etc.

In the recent years, international biological liquid fuel technology and industry is in stage of upgrading and transforming to non-grain raw material, and novel biological liquid fuel using cellulose-like biomass as raw material is greatly developed. Owing to shortcomings of complex conversion, high investment cost, low utilization rate, low ethanol yield, etc. of cellulose raw material, the industrial and commercial applications of cellulose ethanol technology are still in trouble. At the same time, other various novel biological liquid fuels are limited as their immature production technologies and remarkable high production costs compared with gasoline, diesel oil and other petroleum fuels.

Dialkyl carbonate, called carbonic acid dialkyl ester as well, it includes alkoxy and carbonyl in the molecule which is capable to react with a plurality of alcohols, phenols, amines and esters. The dialkyl carbonate is an organic compound which has extremely wide application, high industrial application value and market prospect. The main process for producing the dialkyl carbonate includes phosgene synthesis, oxidative carbonylation, ester exchange, etc. The phosgene synthesis is generally adopted by the conventional industrial production of dialkyl carbonate, since the phosgene and intermediate product of the process are hyper-toxic materials, the byproduct has strong corrosion, the process has caused serious pollution of the environment and is gradually replaced by methanol oxidative carbonylation.

CN101234965B discloses a method for producing dialkyl carbonate. The invention performed a liquid-phase oxidative carbonylation reaction using a catalytic system consisting of an organic halogenated metallic catalyst and at least one catalysis promoter containing nitrogen atom in the presence of alcohol, carbon monoxide and oxygen to produce dialkyl carbonate. Though the method reduces corrosion on the reactor to a certain degree, shortcomings of high price, low conversion rate and selectivity of the catalyst still exist.

As a technology of generating a new ester by exchanging acyl between an ester and another fatty acid, alcohol or ester under a certain condition, the ester exchange technology had many advantages such as wide range of catalyst, moderate reacting condition, easy control of the process, high conversion rate, high quality of the product, etc. CN1699328A discloses a method for preparing dialkyl carbonate; it adopts dimethyl carbonate which is a green chemical raw material and with performance of clean, non-toxic and environmental-friendly to react with aliphatic monohydric alcohol to synthesize dialkyl ester. The method is carried out under moderate reacting conditions; in particular it is able to be produced by renewable biomass resource and is free from three-waste pollution in the producing process. However, the ester exchange reaction uses alcoholate or hydroxide of alkali metals or alkaline-earth metals, alkali carbonate, alkaline-earth carbonate, organic tin, organic zinc or alkaline resin as catalyst, the reacting rate of the process is low and the activity and selectivity is limited.

Besides dimethyl carbonate, cyclic carbonate can also be adopted as initial raw material to prepare dialkyl carbonates. CN102464587A discloses a method for preparing small molecular dialkyl carbonate by ester exchange; the invention adopts cyclic carbonate (such as ethylene carbonate, propylene carbonate and glycerol carbonate) and small molecular alcohol as raw materials and performs the reaction under normal pressure or reduced pressure in the presence of catalyst to prepare the dialkyl carbonate. The method has the advantages of moderate reacting condition, easy separation of catalyst, etc., and with the value of practical application.

Furthermore, furfuryl alcohol is an important organic chemical raw material and with very wide use. At present, it is mainly used for synthesis of resin with various functions, cold-resistant plasticizer, fiber, rubber and pharmaceutical, etc, it can also be used as solvent and rocket fuel, etc. Furfuryl alcohol is mainly obtained by catalytic hydrogenation of furfural, while furfural as the raw material can be obtained by cheap agricultural production. Two-thirds of the produced furfural in the world is used to produce furfuryl alcohol, and China is one of the countries with the most yield of furfural, and the annual output is about 100 thousands. While the furfural which used for the production of furfuryl alcohol only accounts for only about 5% of the total output, and 80% of the furfural is used for cheap exports. Therefore using of carbonate and alcohol which are abundant, green and cheap to develop liquid fuel with economic value and social benefit has important significance.

The present invention adopts dimethyl carbonate or cyclic carbonate which is produced by taking agricultural and forestry wastes as raw material as raw material for producing a liquid fuel, which participates in ester exchange reaction with monohydric alcohol or furfuryl alcohol to produce a series of carbonate products, such as ethyl methyl carbonate, diethyl carbonate, dipropyl carbonate, dibutyl carbonate, high carbon alcohol carbonate, etc. These products are free from toxicity, biodegradable and environmental-friendly, they contain the same carbons with gasoline, diesel oil and kerosene, so they have similar burning calorific value with them. In addition, owing to their special chemical structures, these products are more excellent than fossil-based liquid fuels in performance of lubrication, discharge, noise reduction, volatility, safety, environmental friendliness, etc., and they are also more excellent than biological liquid fuels in performance of low temperature, sealing material compatibility, thermal and oxidizing stabilities, corrosiveness, cost, etc. The liquid fuels are capable of effectively inhibiting corrosion and abrasion of equipment so as to prolong service lives of engine and metal parts. The novel liquid fuels are not reported in the international field at the present time.

DISCLOSURE OF THE INVENTION

The primary objective of the present invention is to provide a liquid fuel which is non-toxic, clean to burn, good in lubrication, good in oxidation stability and environmental-friendly corresponding to the problems of the prior art, the liquid fuel of the present invention has similar burning calorific value to gasoline, diesel oil and kerosene and has high comprehensive cost-effective ratio. The function of the liquid fuel is more excellent than the traditional liquid fuels in all aspects, and it can effectively inhibit corrosion and abrasion of equipment so as to prolong the service lives of the engine and the metal parts.

To achieve the above objects, one aspect of the present invention is to provide a liquid fuel, comprising dialkyl carbonates with the structural formula of

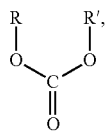

wherein R and R' are same or different, and R and R' are selected from the group consisting of C1-C8 linear chain alkyl, C3-C8 branched chain alkyl, C3-C8 naphthene base and alkyl containing furan ring.

Wherein, the C1-C8 linear chain alkyl is preferably selected from the group consisting of ethyl, propyl, butyl, amyl and octyl; the C3-C8 branched chain alkyl is preferably selected from the group consisting of isopropyl and isobutyl; C3-C8 naphthene base is preferably selected from the group consisting of cyclopropyl and cyclobutyl; and the alkyl containing furan ring is preferably furfuryl alcohol base.

Particularly, when R and R' are furfuryl alcohol base, the dialkyl carbonate is difurfuryl carbonate, which with the structural formula of

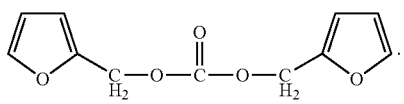

Specifically, the liquid fuel is a mixture of dialkyl carbonates with the structural formula of

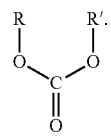

Wherein, in the liquid fuel, total volume percentage of dialkyl carbonates containing carbon atoms no more than 5 is in the range of 60% to 100%, and total volume percentage of dialkyl carbonates containing carbon atoms of 6 to 9 is in the range of 0% to 40%.

Particularly, the dialkyl carbonates containing carbon atoms no more than 5 are selected from one or more of the group consisting of ethyl methyl carbonate and diethyl carbonate, preferably diethyl carbonate; and the dialkyl carbonates containing carbon atoms of 6 to 9 are selected from one or more of the group consisting of dipropyl carbonate, dibutyl carbonate, ethyl propyl carbonate and propyl butyl carbonate, preferably dipropyl carbonate and dibutyl carbonate.

Particularly, total volume percentage of ethyl methyl carbonate and diethyl carbonate in the liquid fuel is in the range of 60% to 100%, wherein volume percentage of ethyl methyl carbonate is preferably in the range of 0% to 10%, more preferably in the range of 5% to 10%, volume percentage of diethyl carbonate is preferably in the range of 50% to 80%, and total volume of dipropyl carbonate and dibutyl carbonate is in the range of 0% to 40%, preferably in the range of 0% to 20%.

Specifically, the liquid fuel with the above components and volume percentage thereof can be used as gasoline or gasoline component, which is to say the liquid fuel can be independently used as gasoline or mixed with other gasoline component to form the blended gasoline.

Wherein, in the liquid fuel, total volume percentage of dialkyl carbonates containing carbon atoms no more than 5 is in the range of 10% to 20%, total volume percentage of dialkyl carbonates containing carbon atoms of 6 to 9 is in the range of 40% to 60%, and total volume percentage of dialkyl carbonates containing carbon atoms of 10 to 17 is in the range of 20% to 30%.

Particularly, the dialkyl carbonates containing carbon atoms no more than 5 are selected from one or more of the group consisting of ethyl methyl carbonate and diethyl carbonate, preferably diethyl carbonate; the dialkyl carbonates containing carbon atoms of 6 to 9 are selected from one or more of the group consisting of dipropyl carbonate, dicyclopropyl carbonate, dibutyl carbonate, diisobutyl carbonate, ethyl propyl carbonate and propyl butyl carbonate, preferably dipropyl carbonate and dibutyl carbonate; the dialkyl carbonates containing carbon atoms of 10 to 17 (namely high carbon alcohol carbonates) are preferably selected from dialkyl carbonates containing carbon atoms of 10 to 13, more preferably diamyl carbonate and dihexyl carbonate.

Particularly, in the liquid fuel, total volume percentage of ethyl methyl carbonate and diethyl carbonate is in the range of 10% to 20%, wherein volume percentage of ethyl methyl carbonate is in the range of 0% to 10% and volume percentage of diethyl carbonate is in the range of 0% to 20%; total volume of dipropyl carbonate and dibutyl carbonate is in the range of 40% to 60%, wherein volume percentage of dibutyl carbonate is in the range of 30% to 60%; and total volume percentage of high carbon alcohol carbonates is in the range of 20% to 30%.

Specifically, the liquid fuel with the above components and volume percentage thereof can be used as diesel oil or diesel oil component.

Wherein, in the liquid fuel, total volume percentage of dialkyl carbonates containing carbon atoms no more than 5 is in the range of 20% to 40%, total volume percentage of dialkyl carbonates containing carbon atoms of 6 to 9 is in the range of 40% to 60%, and total volume percentage of dialkyl carbonates containing carbon atoms of 10 to 17 is in the range of 10% to 20%.

Particularly, the dialkyl carbonates containing carbon atoms no more than 5 are selected from one or more of the group consisting of ethyl methyl carbonate and diethyl carbonate, preferably diethyl carbonate; the dialkyl carbonates containing carbon atoms of 6 to 9 are selected from one or more of the group consisting of dipropyl carbonate, dicyclopropyl carbonate, dibutyl carbonate, diisobutyl carbonate, ethyl propyl carbonate and propyl butyl carbonate, preferably dipropyl carbonate and dibutyl carbonate; the dialkyl carbonates containing carbon atoms of 10 to 17 (namely high carbon alcohol carbonates) are preferably selected from dialkyl carbonates containing carbon atoms of 10 to 13, more preferably diamyl carbonate, dihexyl carbonate and Diheptyl carbonate.

Particularly, in the liquid fuel, total volume percentage of ethyl methyl carbonate and diethyl carbonate is in the range of 20% to 40%, wherein volume percentage of ethyl methyl carbonate is in the range of 0 to 10%, preferably in the range of 1% to 3%, and volume percentage of diethyl carbonate is in the range of 20% to 30%; total volume of dipropyl carbonate and dibutyl carbonate is in the range of 40% to 60%, preferably in the range of 50% to 60%, more preferably 60%; and total volume percentage of high carbon alcohol carbonates is in the range of 10% to 20%, preferably 15%.

Specifically, the liquid fuel with the above components and volume percentage thereof can be used as kerosene or kerosene component.

Another aspect of the present invention is to provide a process of for the production of the liquid fuel, wherein the liquid fuel is produced by ester exchange reaction between carbonate and monohydric alcohol.

Wherein, the carbonate is selected one or more of the group consisting of dimethyl carbonate and cyclic carbonate, the monohydric alcohol is selected from one or more of the group consisting of C1-C8 linear chain alcohol, C3-C8 branched chain alcohol, C3-C8 cyclic alcohol and alcohol containing furan ring.

Particularly, the cyclic carbonate is ethylene carbonate or 1,4-pentanediol carbonate with the structural formula of

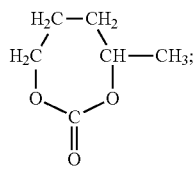

the C1-C8 linear chain alcohol is preferably selected from the group consisting of ethanol, n-propyl alcohol, n-butanol, n-amyl alcohol and n-caprylic alcohol; the C3-C8 branched chain alcohol is preferably selected from the group consisting of isopropyl alcohol and isobutanol; the C3-C8 cyclic alcohol is preferably selected from the group consisting of cyclopropyl alcohol and cyclobutanol; and the alcohol containing furan ring is preferably furfuryl alcohol.

Specifically, when a single monohydric alcohol is adopted in the ester exchange reaction, symmetrical dialkyl carbonate is produced; while when a mixture of monohydric alcohols is adopted, mixture consisting of symmetrical dialkyl carbonates and asymmetrical dialkyl carbonates is produced.

Wherein, the ester exchange reaction is performed in the presence of catalyst, and the catalyst is selected from the group consisting of alkaline catalyst and metal-earth oxide composite catalyst.

Particularly, the weight ratio of the catalyst to the carbonate is in the range of 0.1:100 to 5:100, the mole ratio of the carbonate to the monohydric alcohol is in the range of 1:1 to 1:20, and the ester exchange reaction is performed at a temperature in the range of 60° C. to 300° C. and under an absolute pressure in the range of 0.1 MPa to 8 MPa for 5 minutes to 300 minutes.

Specifically, the alkaline catalyst could be homogeneous catalyst, such as alkali metal carbonate or alkali metal organic salt, and it could also be multi-phase catalyst, such as solid alkaline catalyst, etc. The alkaline catalyst is preferably zinc acetate.

Preferably, when the carbonate of the ester exchange reaction is selected from one or more of the group consisting of dimethyl carbonate and ethylene carbonate and the monohydric alcohol is selected from one or more of the group consisting of C1-C8 linear chain alcohol, C3-C8 branched chain alcohol and C3-C8 cyclic alcohol, the alkaline catalyst is adopted. In this case, the weight ratio of the alkaline catalyst to the carbonate is in the range of 0.1:100 to 5:100, preferably in the range of 0.1:100 to 1:100; the mole ratio of the carbonate to the monohydric alcohol is in the range of 1:2 to 1:8; the ester exchange reaction is performed at a temperature in the range of 60° C. to 200° C. and under an absolute pressure in the range of 0.1 MPa to 8 MPa for 10 minutes to 300 minutes, preferably at a temperature in the range of 140° C. to 200° C. and under an absolute pressure in the range of 2 MPa to 8 MPa for 10 minutes to 20 minutes. Performing at the above high temperature and under the above high pressure makes that the time of the ester exchange reaction is short and the catalyst dosage is low, and the conversion rate of dimethyl carbonate or the ethylene carbonate is 100%.

Wherein, the metal-earth oxide composite catalyst includes metallic oxide and rare earth oxide, the weight ratio of the metallic oxide to the rare earth oxide is (90-99):(1-10); the metallic oxide is selected from one or more of the group consisting of zinc oxide, aluminum oxide and stannous oxide and the rare earth oxide is selected from one or more of the group consisting of lanthanum oxide and cerium oxide. Particularly, the metallic oxide consists of zinc oxide, aluminum oxide and stannous oxide. The weight ratio between zinc oxide, aluminum oxide and stannous oxide in the metal-earth oxide composite catalyst is (6-8):(1-2):(1-2), and the rare earth oxide includes lanthanum oxide and cerium oxide. Reduce the metal-earth oxide composite catalyst in particular at a temperature of 200° C. for 2 hours to 10 hours, preferably for 4 hours to 6 hours.

Wherein, the metal-earth oxide composite catalyst is prepared by coprecipitation and impregnation which are conventional in the Art. In particular, the metal-earth oxide composite catalyst is prepared by the following steps:

a) adding precipitant into the metal nitrate solution/mixed solution to form precipitation, then drying or baking the precipitation to obtain metallic oxide;

b) dipping the metallic oxide into the rare earth nitrate solution, then drying and baking to obtain the metal-earth oxide composite catalyst.

Specifically, the precipitant is carbonate solution, preferably sodium carbonate solution, more preferably sodium carbonate solution of 1 mol/L; the drying is performed at a temperature in range of 100° C. to 150° C. for 8 hours to 24 hours, preferably at 120° C. for 12 hours; the baking is performed at a temperature in range of 400° C. to 600° C. for 2 hours to 5 hours, preferably at 500° C. for 3 hours.

Preferably, when the carbonate of the ester exchange reaction is selected from one or more of the group consisting of dimethyl carbonate and ethylene carbonate and the monohydric alcohol is furfuryl alcohol, the metal-earth oxide composite catalyst is adopted. In this case, the mole ratio of the carbonate to furfuryl alcohol is in the range of 1:1 to 1:20, preferably in the range of 1:2 to 1:8; the ester exchange reaction is performed at a temperature in the range of 100° C. to 300° C. and under an absolute pressure in the range of 1.5 MPa to 8 MPa for 5 minutes to 300 minutes, preferably at a temperature in the range of 120° C. to 200° C. and under an absolute pressure in the range of 2 MPa to 4 MPa for 5 minutes to 100 minutes, preferably for 10 minutes to 40 minutes. Specifically, conversion rate of dimethyl carbonate in the ester exchange reaction is not lower than 85%, preferably not lower than 95%, and difurfuryl carbonate yield is not lower than 80%, preferably not lower than 90%.

Preferably, when the carbonate of the ester exchange reaction is 1,4-pentanediol carbonate and the monohydric alcohol is selected from one or more of the group consisting of C1-C8 linear chain alcohol, C3-C8 branched chain alcohol, C3-C8 cyclic alcohol and alcohol containing furan ring, the metal-earth oxide composite catalyst is adopted. In this case, the monohydric alcohol is excessive corresponding to 1,4-pentanediol carbonate; specifically, the mole ratio of 1,4-pentanediol carbonate to the monohydric alcohol is 1:1 to 1:20, preferably 1:4 to 1:20, more preferably 1:6 to 1:8; the weight ratio of the metal-rare earth composite catalyst to the total weight of 1,4-pentanediol carbonate and the monohydric alcohol is 0.1:100 to 5:100, preferably 0.1:100 to 2:100, more preferably 0.1:100 to 1:100; the ester exchange reaction is performed at a temperature in the range of 120° C. to 180° C. under an absolute pressure in range of 0.1 MPa to 4 MPa for 5 minutes to 120 minutes, preferably performed at a temperature in the range of 150° C. to 160° C. and under an absolute pressure in range of 2 MPa to 3 MPa for 5 minutes to 30 minutes, more preferably for 20 minutes to 30 minutes.

Particularly, 1,4-pentanediol carbonate is produced by a cycloaddition reaction between 2-methyl tetrahydrofuran and carbon dioxide.

Wherein, the cycloaddition reaction is performed in the presence of magnesium-zinc-rare earth oxide composite catalyst; the magnesium-zinc-rare earth oxide composite catalyst includes magnesium oxide, zinc oxide and rare earth oxide; the mole ratio of magnesium oxide to zinc oxide is 1:1 to 4:1, preferably 1:1 to 3:1, more preferably 1.5:1; the mass percentage of the rare earth oxide in the magnesium-zinc-rare earth oxide composite catalyst is in the range of 0.1% to 1%, preferably 0.6% to 1%, more preferably 0.8%; and the rare-earth oxide is preferably selected from one or more of the group consisting of lanthanum oxide and cerium oxide.

Wherein, the magnesium-zinc-rare earth oxide composite catalyst is prepared by coprecipitation and impregnation which are conventional in the Art. More specifically, preparing the magnesium oxide-zinc oxide composite by coprecipitation firstly, and then further compounding rare-earth oxide on the magnesium oxide-zinc oxide composite by impregnation. Reduce the magnesium-zinc-rare earth oxide composite catalyst at 200° C. for 2 hours to 10 hours before use, preferably for 4 hours to 6 hours.

Particularly, the process for preparing the magnesium-zinc-rare earth oxide composite catalyst comprising the following steps:

1) heating a mixed solution containing magnesium nitrate and zinc nitrate, adding a precipitant therein, then regulating pH value, insulating heat and aging, after filtering and drying, magnesium oxide-zinc oxide compound is obtained;

2) dipping a rare earth solution on the magnesium oxide-zinc oxide compound, after drying and baking, the magnesium-zinc-rare earth oxide composite catalyst is obtained.

Wherein, in the step 1), the concentration of the mixing solution is 1 mol/L; the heating is performed at a temperature in the range of 40° C. to 60° C., preferably 45° C.; the aging lasts for 1 hour to 4 hours, preferably 2 hours; the pH value is regulated to 8 to 9; the drying is performed at a temperature in the range of 100° C. to 150° C., preferably 110° C.; the drying lasts for 8 hours to 24 hours, preferably 12 hours; the precipitant is $Na_2CO_3$ solution of 1 mol/L; and the addition of the precipitant lasts for about 30 minutes.

Particularly, in the step 2), the dipping lasts for 8 hours to 24 hours, preferably 12 hours; the drying is performed at a temperature in the range of 100° C. to 150° C., preferably at 110° C.; the drying lasts for 2 hours to 5 hours, preferably 3 hours; the baking is performed at a temperature in the range of 400° C. to 600° C., preferably at 500° C.; and the baking lasts for 2 hours to 5 hours, preferably 3 hours.

Wherein, in the cycloaddition reaction, the carbon dioxide is excessive corresponding to 2-methyl tetrahydrofuran; specifically, the mole ratio of 2-methyl tetrahydrofuran to carbon dioxide is 1:1 to 1:20, preferably 1:8 to 1:15, more preferably 1:10 to 1:12; the weight ratio of the magnesium oxide-zinc oxide compound rare-earth oxide to 2-methyl tetrahydrofuran is 0.1:100 to 5:100, preferably 0.1:100 to 2:100, more preferably 0.1:100 to 1:100. Furthermore, the temperature of the cycloaddition reaction is in the range of 80° C. to 150° C., preferably 110° C. to 130° C.; the absolute pressure is in range of 2 MPa to 10 MPa, preferably 2 MPa to 8 MPa, more preferably 5 MPa to 8 MPa; and the reaction time is in the range of 5 minutes to 120 minutes, preferably 5 minutes to 30 minutes, more preferably 20 minutes to 30 minutes.

Particularly, the raw material of the present invention is preferably produced by taking biomass as raw material.

Such as, dimethyl carbonate or ethylene carbonate could be produced by taking biomass as raw material as follows: firstly, directly fermenting the biomass raw material such as sugar crops including sugar cane, beet, sweet sorghum and starch crops including cassava, potato, corn to produce ethanol, ethanol is dehydrated to produce ethylene, ethylene is oxidized to produce epoxyethane, following epoxyethane is reacted with carbon dioxide to produce ethylene carbonate, and then performing an ester exchange reaction between ethylene carbonate and methanol to produce dimethyl carbonate.

Furfuryl alcohol or 2-methyl tetrahydrofuran could be produced by taking biomass as raw material as follows: firstly, performing an acid hydrolysis reaction to the waste biomass to obtain furfural, following furfural is reduced to produce furfuryl alcohol, and then performing a hydrogenation reaction between furfural and hydrogen to produce 2-methyl tetrahydrofuran (which has been disclosed in CN102558106A), in particular comprising the steps of:

A1) performing an acid hydrolysis reaction to the waste biomass to obtain furfural and acetylpropionic acid;

A2) performing a hydrogenation reaction between furfural and hydrogen to obtain 2-methyl tetrahydrofuran.

Wherein, in the step A1), concentrated sulfuric acid is adopted to perform the acid hydrolysis reaction to the waste biomass; the process of the acid hydrolysis has two steps which includes the first step of acid hydrolysis and the second step of acid hydrolysis, wherein the first step of acid hydrolysis is performed at a temperature in range of 200° C. to 260°

C. and under an absolute pressure in range of 1.8 Mpa to 2.6 Mpa for 10 minutes to 20 minutes; and the second step of acid hydrolysis is performed at a temperature in range of 180° C. to 220° C. and under an absolute pressure in range of 1.0 Mpa to 1.6 Mpa for 15 minutes to 20 minutes.

Wherein, the process of the hydrogenation reaction in the step A2) includes two steps. In the first step, the mole ratio of hydrogen to furfural is 40:1 to 60:1, the mass space velocity of hydrogen is $10\ h^{-1}$ to $20\ h^{-1}$, and the first step of hydrogenation is performed at a temperature in range of 180° C. to 240° C. and under an absolute pressure in range of 1 MPa to 4 MPa for 1 minute to 3 minutes. In the second step, the mole ratio of hydrogen to furfural is 40:1 to 60:1, the mass space velocity of hydrogen is $10\ h^{-1}$ to $20\ h^{-1}$, and the second step of hydrogenation is performed at a temperature in range of 190° C. to 210° C. and under an absolute pressure in range of 4 MPa to 6 MPa for 1 minute to 3 minutes.

Particularly, the first step of hydrogenation reaction is performed in the presence of copper-chrome-cerium-lanthanum composite catalyst; the copper-chrome-cerium-lanthanum composite catalyst consists of copper oxide, chromium sesquioxide, cerium oxide and lanthanum oxide which mass percentage respectively in the range of 40% to 60%, 30% to 40%, 5% to 10% and 5% to 10% in the composite catalyst.

Particularly, the second step of hydrogenation reaction is performed in the presence of nickel-aluminium composite catalyst; the nickel-aluminium composite catalyst includes nickel oxide and aluminium oxide which mass percentage respectively in the range of 60% to 80% and 20% to 40% in the composite catalyst.

Wherein, the agricultural and forestry waste includes shrub wood stubbles of yellow willow, salix mongolica, caragana microphylla, etc., crop straws of soybean straw, maize straw, etc., agricultural wastes of corncob, bagasse, oat shell, cottonseed shell, rice bran shell, sunflower shell, etc., waste sugar and starches, etc.

Particularly, the process further comprises a step of distilling the product of the ester exchange reaction to obtain a liquid fuel.

Wherein, the product is distilled under an absolute pressure in range of 0.01 MPa to 0.02 MPa and at a temperature in range of 180° C. to 220° C., and collecting fractions of 80° C. to 90° C., 125° C. to 135° C. and 180° C. to 200° C. respectively to obtain the liquid fuel.

Specifically, during the distillation, collecting the fraction in the range of 80° C. to 90° C. to obtain dialkyl carbonate mixture containing carbon atoms no more than 5, collecting the fraction in the range of 125° C. to 135 L to obtain dialkyl carbonate mixture containing carbon atoms of 6 to 9, and collecting the fraction in the range of 180° C. to 200° C. to obtain dialkyl carbonate mixture containing carbon atoms of 10 to 17.

Performing an ester exchange reaction between the carbonate and single monohydric alcohol to obtain single dialkyl carbonate, then mixing the single dialkyl carbonate by certain volume percentage to obtain the liquid fuel of the present invention; or performing an ester exchange reaction between the carbonate and mixed monohydric alcohol to obtain a mixture of dialkyl carbonates, then collecting different fractions to obtain the liquid fuel of the present invention Another aspect of the present invention is to provide a process for producing a liquid fuel, comprising the steps of:

A) performing a cycloaddition reaction between 2-methyl tetrahydrofuran and carbon dioxide to produce a cyclic carbonate with the structural formula of

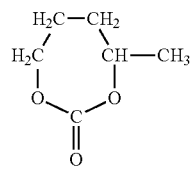

B) performing an ester exchange reaction between the cyclic carbonate and monohydric alcohol to produce the liquid fuel.

Specifically, the 2-methyl tetrahydrofuran is produced by using agricultural and forestry waste as initial raw material.

Another aspect of the present invention is to provide a process for producing a liquid fuel, comprising the steps of:

A) taking agricultural and forestry waste as initial raw material to produce 2-methyl tetrahydrofuran;

B) performing a cycloaddition reaction between the 2-methyl tetrahydrofuran and carbon dioxide to produce a cyclic carbonate with the structural formula of

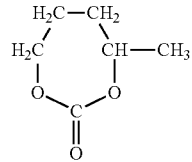

C) performing an ester exchange reaction between the cyclic carbonate and monohydric alcohol to produce the liquid fuel.

Another aspect of the present invention is to provide a cyclic carbonate with the structural formula of

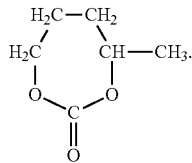

Another aspect of the present invention is to provide application of the cyclic carbonate with the structural formula of

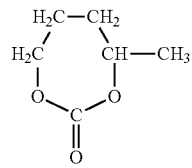

in producing cyclic carbonate, wherein the cyclic carbonate participates in ester exchange reaction with monohydric alcohol to produce the liquid fuel.

Another aspect of the present invention is to provide an application of dialkyl carbonates prepared by the said process in liquid fuel, such as the dialkyl carbonates could be used as gasoline or gasoline component, diesel oil or diesel oil component, kerosene or kerosene component.

Another aspect of the present invention is to provide an application of difurfuryl carbonate in liquid fuel, lubricant and engineering plastic.

Wherein, when the difurfuryl carbonate is applied to liquid fuel, it has high oxygen content to ensure complete combustion. The difurfuryl carbonate can be directly used as diesel oil, and its quality is accordant with related regulation of national standard GB/T19147-2003. The difurfuryl carbonate can be directly used as kerosene, and its quality is accordant with related regulation of ASTMD910. The difurfuryl carbonate can also be used as liquid fuel additive, when added in gasoline or diesel oil, it can improve octane number of the gasoline, cetane number of diesel oil as well as lubrication and discharge performance of the petroleum fuel.

Wherein, when the difurfuryl carbonate is applied to lubricant, its performance is similar to lubricants such as high carbon alcohol carbonate. Furthermore, it has performance of low friction and resistance, moderate viscosity, good oxidizing and thermal stabilities, good compatibility with rubber sealing material, abrasion resistance, self-cleaning, low corrosion, low residual carbon, high oil film intensity, etc. and can be used as internal combustion engine oil, compressor oil, freezer oil, hydraulic oil, etc.

Wherein, when the difurfuryl carbonate is applied to engineering plastic, it could be used as engineering plastic monomer for producing the polycarbonate. The produced carbonate has performance of excellent thermal stability, creep resistance, cold resistance, electrical insulating property, fire resistance, etc. and can be widely used in the building material industry, automobile manufacturing industry, medical apparatus, aerospace, package, electronic appliance, optical lens and related fields, and it can be applied to disc base material as well.

Another aspect of the present invention is to provide a liquid fuel or liquid fuel additive which including difurfuryl carbonate. Specifically the liquid fuel includes gasoline, diesel oil, kerosene, etc.

Another aspect of the present invention is to provide a lubricant or lubricant component which including difurfuryl carbonate. Specifically the lubricant includes internal combustion engine oil, compressor oil, freezer oil, hydraulic oil, etc.

Another aspect of the present invention is to provide an engineering plastic monomer which including difurfuryl carbonate. Specifically the engineering plastic is polycarbonate.

Compared with the prior art, the invention has the following advantages:

1. The liquid fuel could be produced by waste biomass which with a wide range, low cost and is easy obtained, the process of the invention is featured with simple producing process, short producing cycle and low energy consumption which is beneficial for a large scale industrial production, furthermore, the speed of the reaction is quick, the conversion rate and selectivity of the substrate and the yield of product are high, the economic and social benefit is remarkable.

2. The liquid fuel is free from toxicity and is biodegradable, it integrates advantages of conventional fossil-based and biological liquid fuels; the liquid fuel is more excellent than fossil-based liquid fuel in performance of lubrication, discharge, noise reduction, volatility, safety, environmental friendliness, etc., and it is more excellent than biological liquid fuel in performance of low temperature, sealing material compatibility, thermal and oxidizing stabilities, corrosiveness, cost, etc.; the liquid fuel is capable of effectively inhibiting corrosion and abrasion of equipment, which is beneficial for prolonging service lives of engine and metal parts.

3. The liquid fuel of the present invention is similar to the gasoline, diesel oil and kerosene in burning calorific value, and its quality is accordant with regulations of related national standards; the liquid fuel can be used to replace the existing petroleum liquid fuels (such as gasoline, diesel oil, kerosene, etc.), biological liquid fuels (such as biological diesel oil, biological gasoline, biological kerosene, etc.) and other fuels (such as cooking, heating fuels, etc.), and the application range of the liquid fuel is wide.

MODE OF CARRYING OUT THE INVENTION

The invention will be further described by the following concrete embodiments, and the advantages and features of the invention will be clearer. However the embodiments are only demonstrative and have no limitation on the scope of the invention. The person skilled in the Art shall understand that the technical solution of the invention can be modified or replaced in both detail and form under a precondition of not deviating from spirit and scope of the invention, but the modifications and replacements shall be included in the protection scope of the invention.

Embodiment 1

Single Ester Exchange Reaction Between Dimethyl Carbonate (or Ethylene Carbonate) and Monohydric Alcohol Performing ester exchange reaction between dimethyl carbonate (or ethylene carbonate) and single monohydric alcohol containing 2 to 8 carbon atoms in the presence of zinc acetate as catalyst in a tubular ester exchange reactor; in the reaction, the weight ratio of zinc acetate to dimethyl carbonate or ethylene carbonate is 0.1:100 to 1:100, and the mole ratio of dimethyl carbonate (or ethylene carbonate) to monohydric alcohol 1:2 to 1:8; the reaction is carried out at a temperature in the range of 140° C. to 200° C. and under an absolute pressure in the range of 2 MPa to 8 MPa for 10 minutes to 20 minutes to obtain the reaction product.

Distilling the reaction product under an absolute pressure in the range of 0.01 MPa to 0.02 MPa and at a temperature in the range of 180° C. to 200° C., then collecting corresponding fraction to obtain dialkyl carbonate containing different carbon atoms, wherein the volume percentage of the dialkyl carbonate in each fraction is not less than 95%.

Embodiment 2

Mixed Ester Exchange Reaction Between Dimethyl Carbonate (or Ethylene Carbonate) and Monohydric Alcohol Mixing dimethyl carbonate (or ethylene carbonate) with a mixture of monohydric alcohols containing 2 to 8 carbon atoms to form a reaction mixture, putting the reaction mixture in a tubular ester exchange reactor to perform an ester exchange reaction, the dialkyl carbonate mixture is obtained after the reaction, and the conditions of the ester exchange reaction refer to Embodiment 1.

Distilling the dialkyl carbonate mixture under an absolute pressure in the range of 0.01 MPa to 0.02 MPa and at a temperature in the range of 180° C. to 200° C., then collecting fraction in the range of 80° C. to 90° C. to obtain dialkyl carbonate mixture containing carbon atoms no more than 5, collecting fraction in the range of 125° C. to 135° C. to obtain dialkyl carbonate mixture containing carbon atoms of 6 to 9, collecting fraction in the range of 180° C. to 200° C. to obtain dialkyl carbonate mixture containing carbon atoms of 10 to 17.

Embodiment 3

Producing Difurfuryl Carbonate from 1,4-Pentanediol Carbonate and Furfuryl Alcohol I. Preparing 2-Methyl Tetrahydrofuran Grinding straw and adding water to obtain biomass slurry in which the content of water is 65%; adding the biomass slurry and concentrated sulfuric acid into a reactor; performing the first step of acid hydrolysis reaction at 200° C. and under 2.2 MPa for 20 minutes to obtain a first product of the first step of acid hydrolysis; flash distilling the first product and then adding into a second reactor, performing the second step of acid hydrolysis reaction at 180° C. and under 1.4 MPa for 15 minutes to obtain a second product, refining the second product to obtain furfural with a purity of 99.2%.

Adding copper-chrome-cerium-lanthanum composite catalyst (including copper oxide, chromium sesquioxide, cerium oxide and lanthanum oxide which mass percentage respectively is 50%, 40%, 5% and 5% in the composite catalyst) and furfural into a first hydrogenation reactor; filling hydrogen into the reactor and performing a first step of hydrogenation reaction at 220° C. under 3 MPa to obtain 2-methyl furan; then adding 2-methyl furan and nickel-aluminum composite catalyst (including 70 wt % of nickel oxide and 30 wt % of aluminum oxide) into a second hydrogenation reactor; performing a second step of hydrogenation reaction at 200° C. under 6 MPa; refining the reaction product to obtain 2-methyl tetrahydrofuran with a purity of 96%.

II. Performing a Cycloaddition Reaction

1. Preparing Magnesium-Zinc-Rare Earth Oxide Composite Catalyst

By a coprecipitation method, stirring and increasing mixed metal solution containing magnesium nitrate and zinc nitrate to 45° C.; slowly adding $Na_2CO_3$ solution therein for about 30 minutes, regulating pH value to 8 to 9, aging for 2 hours at 45° C.; after standing, filtering and washing, drying for 12 hours at 110° C. to obtain magnesium oxide-zinc oxide compound, wherein the mole ratio of magnesium oxide to zinc oxide is 1.5:1.

By an impregnation method, dipping mixed rare earth solution containing lanthanum nitrate and cerium nitrate on the magnesium oxide-zinc oxide compound for 12 hours, drying for 3 hours at 110° C., and then baking for 3 hours at 500° C. to obtain magnesium-zinc-rare earth oxide composite catalyst, wherein the mole ratio of the lanthanum element to cerium element is 1:1.

The prepared composite catalyst includes magnesium oxide, zinc oxide, lanthanum oxide and cerium oxide, wherein the mole ratio of magnesium element to zinc element is 1.5:1, the mole ratio of lanthanum element to cerium element is 1:1; and the total weight of lanthanum oxide and cerium oxide counts for 0.8% of the entire weight of the composite catalyst; reducing the magnesium-zinc-rare earth oxide composite catalyst for 6 hours by hydrogen at 200° C. before use.

2. Performing a Cycloaddition Reaction

Adding 2-methyl tetrahydrofuran and the prepared magnesium-zinc-rare earth oxide composite catalyst into a reactor at the weight ratio of 100:0.5; opening a heating device to keep the temperature of rector constant at 120° C.; filling excessive $CO_2$ into the reactor and controlling an absolute pressure in the reactor under 8.0 MPa; then performing a cycloaddition reaction between 2-methyl tetrahydrofuran and $CO_2$ in the reactor for 30 minutes to obtain the reaction product, distilling the product to obtain 1,4-pentanediol carbonate, wherein the mole ratio of 2-methyl tetrahydrofuran to $CO_2$ is 1:10, conversion rate of 2-methyl tetrahydrofuran in the cycloaddition reaction is 90%, and yield of the 1,4-pentanediol carbonate is 60%.

Reaction equation of the cycloaddition reaction is as follows:

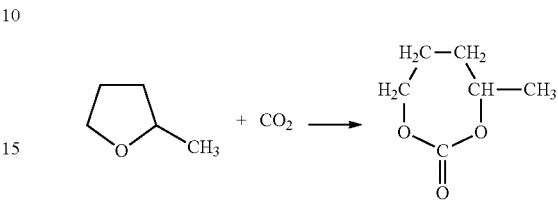

III. Performing Ester Exchange Reaction

1. Preparing Metal-Rare Earth Oxide Composite Catalyst

By a coprecipitation method, dissolving zinc nitrate, aluminum nitrate and stannous nitrate in distilling water; mixing uniformly to obtain zinc-aluminum-tin mixed solution; dropping the zinc-aluminum-tin mixed solution and sodium carbonate solution into a container containing distilling water of 60° C. under a stirring condition at the same time to obtain a dropping liquid, regulating dropping speeds of zinc-aluminum-tin mixed solution and sodium carbonate solution to keep pH value of the dropping liquid at 7 to 8 during dropping; after dropping, depositing and aging the dropping liquid for 2 hours, following washing, filtering and drying for 12 hours at 120° C., and then roasting for 3 hours at 500° C. to obtain $ZnO$—$Al_2O_3$—$SnO_2$ metallic catalyst;

By an impregnation method, dissolving lanthanum nitrate $(La(NO_3)_3 \cdot 6H_2O)$ and cerium nitrate $(Ce(NO_3)_3 \cdot 6H_2O)$ in the distilling water to obtain rare earth mixed solution; dipping the $ZnO$—$Al_2O_3$—$SnO_2$ metallic catalyst in the rare earth mixed solution to obtain impregnation mixture; drying the impregnation mixture for 12 hours at 120° C., roasting for 3 hours at 500° C., then grinding and sieving 20 to 40 meshes to obtain metal-rare earth oxide composite catalyst.

In the metal-rare earth oxide composite catalyst, mass percentages of various oxides are respectively as follows: 60% of zinc oxide, 20% of aluminum oxide, 15% of stannous oxide, 2.5% of lanthanum oxide and 2.5% of cerium oxide; reducing the metal-rare earth oxide composite catalyst for 6 h by hydrogen at 200° C. before use.

2. Performing an Ester Exchange Reaction:

Adding 1,4-pentanediol carbonate and furfuryl alcohol in a tubular ester exchange reactor; then adding the prepared metal-rare earth oxide composite catalyst, mixing uniformly and performing an ester exchange reaction, distilling the reaction product to obtain difurfuryl carbonate, wherein the mole ratio of 1,4-pentanediol carbonate to furfuryl alcohol is 1:6, and the weight ratio of the metal-rare earth oxide composite catalyst to the total weight of 1,4-pentanediol carbonate and furfuryl alcohol is 0.5:100; the ester exchange reaction is performed at a temperature of 160° C. and under an absolute pressure of 3 MPa for 20 minutes; in the ester exchange reaction, the conversion rate of 1,4-pentanediol carbonate is 100%, and yield of difurfuryl carbonate is 92%.

Reaction equation of the ester exchange reaction is as follows:

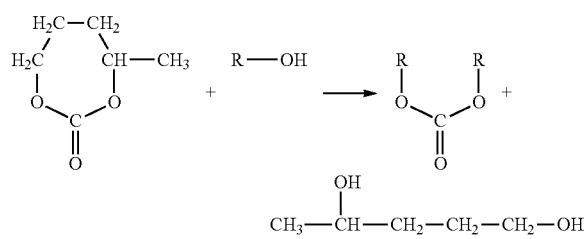

Testing calorific value by D4529, testing cetane number by D2700, testing closed-cup flash point by GB/T261, testing kinematic viscosity at 40° C. by GB/T265, testing pour point by GB/T3535, testing oxidation stability at 110° C. by EN14112, testing corrosion performance of copper sheet at 50° C. by D120 and testing sealing adaptability performance index by SG/T0305.

Calorific value of difurfuryl carbonate is 39.8 MJ/kg, cetane number is 97, closed-cup flash point is 158° C., kinematic viscosity at 40° C. is 22.6 mm²/s, pour point is −21° C., oxidation stability at 110° C. is 30, corrosion performance of copper sheet is 1 grade, and sealing adaptability performance index is 4.

Embodiment 4

Producing Difurfuryl Carbonate from Dimethyl Carbonate and Furfuryl Alcohol

Adding dimethyl carbonate and furfuryl alcohol in a tubular ester exchange reactor; then adding the metal-rare earth oxide composite catalyst prepared by the embodiment 1, mixing uniformly and performing an ester exchange reaction, then distilling the reaction product to obtain difurfuryl carbonate, wherein the mole ratio of 1,4-pentanediol carbonate to furfuryl alcohol is 1:6, and the weight ratio of the metal-rare earth oxide composite catalyst to the total weight of dimethyl carbonate and furfuryl alcohol is 0.5:100; the ester exchange reaction is performed at a temperature of 160° C. and under an absolute pressure of 3 MPa for 20 minutes; in the ester exchange reaction, the conversion rate of dimethyl carbonate is 95%, and yield of difurfuryl carbonate is 90%.

Calorific value of the produced difurfuryl carbonate is 39.6 MJ/kg, cetane number is 97, closed-cup flash point is 156° C., kinematic viscosity at 40° C. is 22.8 mm²/s, pour point is −20° C., oxidation stability at 110° C. is 30, corrosion performance of copper sheet is 1 grade, and sealing adaptability performance index is 4.

Embodiment 5

Producing Diethyl Carbonate from 1,4-Pentanediol Carbonate and Ethanol

I. Cycloaddition Reaction
Preparing magnesium-zinc-rare earth oxide composite catalyst which includes magnesium oxide, zinc oxide, lanthanum oxide and cerium oxide by coprecipitation and impregnation described in Embodiment 3, wherein the mole ratio of magnesium oxide to zinc oxide is 1:1, and the mole ratio of the lanthanum element to the cerium element is 2:1; the total weight of the lanthanum oxide and the cerium oxide is controlled to count for 1% of the entire weight of the composite catalyst; and reducing the magnesium-zinc-rare earth oxide composite catalyst by hydrogen before use.

Adding 2-methyl tetrahydrofuran prepared by the embodiment 3 and the magnesium-zinc-rare earth oxide composite catalyst into a reactor at the weight ratio of 100:1; opening a heating device to keep temperature of the rector constant at 80° C.; filling excessive $CO_2$ into the reactor, and controlling the absolute pressure in the reactor under 6.0 MPa; performing a cycloaddition reaction between 2-methyl tetrahydrofuran and $CO_2$ in the reactor for 20 minutes to obtain the reaction product, distilling the reaction product to obtain 1,4-pentanediol carbonate, wherein the mole ratio of 2-methyl tetrahydrofuran to $CO_2$ is 1:15, conversion rate of 2-methyl tetrahydrofuran in the cycloaddition reaction is 86%, and yield of 1,4-pentanediol carbonate is 54%.

II. Performing Ester Exchange Reaction
Preparing metal-rare earth oxide composite catalyst by coprecipitation and impregnation described in Embodiment 3, wherein the prepared metal-rare earth oxide composite catalyst comprises zinc oxide, aluminum oxide, lanthanum oxide and cerium oxide which respectively count for 80%, 10%, 5% and 5%; reducing the magnesium-zinc-rare earth oxide composite catalyst by hydrogen before use.

Adding 1,4-pentanediol carbonate and ethanol in a tubular ester exchange reactor; then adding the prepared metal-rare earth oxide composite catalyst, uniformly mixing and performing an ester exchange reaction, then distilling the reaction product to obtain diethyl carbonate, wherein the mole ratio of 1,4-pentanediol carbonate to ethanol is 1:10, and the weight ratio of the metal-rare earth oxide composite catalyst to the total weight of 1,4-pentanediol carbonate and ethanol is 1:100; the ester exchange reaction is performed at a temperature of 180° C. and under an absolute pressure of 2 MPa for 10 minutes; in the ester exchange reaction, the conversion rate of 1,4-pentanediol carbonate is 100%, and yield of diethyl carbonate is 95%.

Embodiment 6

Producing Diisobutyl Carbonate From 1,4-Pentanediol Carbonate and Isobutanol

I. Cycloaddition Reaction
Preparing magnesium-zinc-rare earth oxide composite catalyst which includes magnesium oxide, zinc oxide, lanthanum oxide and cerium oxide by coprecipitation and impregnation described in the embodiment 3, wherein the mole ratio of magnesium oxide to zinc oxide is 2:1, and the mole ratio of the lanthanum element to the cerium element is 3:1; the total weight of lanthanum oxide and cerium oxide is controlled to count for 0.2% of the entire weight of the composite catalyst; reducing the magnesium-zinc-rare earth oxide composite catalyst by hydrogen before use.

Adding 2-methyl tetrahydrofuran prepared by the embodiment 3 and the magnesium-zinc-rare earth oxide composite catalyst into a reactor at the weight ratio of 100:3; opening a heating device to keep temperature of the rector constant at 150° C.; filling excessive $CO_2$ into the reactor, and controlling absolute pressure in the reactor under 2 MPa; performing a cycloaddition reaction between 2-methyl tetrahydrofuran and $CO_2$ in the reactor for 100 minutes to obtain the reaction product, distilling the reaction product to obtain 1,4-pentanediol carbonate, wherein the mole ratio of 2-methyl tetrahydrofuran to $CO_2$ is 1:3, conversion rate of 2-methyl tetrahydrofuran in the cycloaddition reaction is 83%, and yield of the 1,4-pentanediol carbonate is 50%.

II. Ester Exchange Reaction
Preparing metal-rare earth oxide composite catalyst by coprecipitation and impregnation described in the embodiment 3, and the metal-rare earth oxide composite catalyst includes zinc oxide, aluminum oxide, lanthanum oxide and cerium oxide which respectively count for 70%, 15%, 14% and 1%; reducing the magnesium-zinc-rare earth oxide composite catalyst by hydrogen before use;

Adding 1,4-pentanediol carbonate and isobutanol in a tubular ester exchange reactor; then adding the prepared metal-rare earth oxide composite catalyst, uniformly mixing and performing an ester exchange reaction, following distilling the reaction product to obtain diisobutyl carbonate, wherein the mole ratio of 1,4-pentanediol carbonate to isobutanol is 1:4, and the weight ratio of the metal-rare earth oxide composite catalyst to the total weight of the 1,4-pentanediol carbonate and isobutanol is 0.2:100; the ester exchange reaction is performed at a temperature of 120° C. and under an absolute pressure of 4 MPa for 60 minutes; in the ester exchange reaction, the conversion rate of 1,4-pentanediol carbonate is 98%, and yield of diisobutyl carbonate is 92%.

Embodiment 7

Producing Dicyclopropanol Carbonate From 1,4-Pentanediol Carbonate and Cyclopropanol I. Cycloaddition Reaction Preparing magnesium-zinc-rare earth oxide composite catalyst which includes magnesium oxide, zinc oxide, lanthanum oxide and cerium oxide by coprecipitation and impregnation described in the embodiment 1, wherein the mole ratio of magnesium oxide to zinc oxide is 3:1, and the total weight of the lanthanum oxide and the cerium oxide is controlled to count for 0.6% of the entire weight of the composite catalyst; reducing the magnesium-zinc-rare earth oxide composite catalyst by hydrogen before use.

Adding 2-methyl tetrahydrofuran prepared by the embodiment 3 and the magnesium-zinc-rare earth oxide composite catalyst into a reactor at the weight ratio of 100:0.1; opening a heating device to keep temperature of the rector constant at 100° C.; filling excessive $CO_2$ into the reactor, and controlling absolute pressure in the reactor under 10 MPa; performing a cycloaddition reaction between 2-methyl tetrahydrofuran and $CO_2$ in the reactor for 60 minutes to obtain the reaction product, after distilling 1,4-pentanediol carbonate is produced, wherein the mole ratio of 2-methyl tetrahydrofuran to $CO_2$ is 1:8, conversion rate of 2-methyl tetrahydrofuran in the cycloaddition reaction is 85%, and yield of 1,4-pentanediol carbonate is 52%.

II. Ester Exchange Reaction

Adding 1,4-pentanediol carbonate and cyclopropanol in a tubular ester exchange reactor; then adding the metal-rare earth oxide composite catalyst prepared by the embodiment 3, uniformly mixing and performing an ester exchange reaction, distilling the reaction product to obtain dicyclopropanol carbonate, wherein the mole ratio of 1,4-pentanediol carbonate to cyclopropanol is 1:15, and the weight ratio of the metal-rare earth oxide composite catalyst to the total weight of 1,4-pentanediol carbonate and cyclopropanol is 2:100; the ester exchange reaction is performed at a temperature of 140° C. and under an absolute pressure of 0.5 MPa for 120 minutes; in the ester exchange reaction, the conversion rate of 1,4-pentanediol carbonate is 99%, and yield of the dicyclopropanol carbonate is 93%.

Embodiment 8

Producing the Blended Gasoline

Producing ethyl methyl carbonate, diethyl carbonate, dipropyl carbonate and dibutyl carbonate which with volume percentage not less than 95% respectively according to Embodiment 1 (or directly adopting normal commercial dialkyl carbonates), then mixing the dialkyl carbonates according to the composition and the volume percentage in Table 1 to obtain the blended gasoline 8-1 and 8-2.

Performing a mixed ester exchange reaction between dimethyl carbonate (or ethylene carbonate) and the mixture which containing ethanol, n-propyl alcohol and n-butyl alcohol to obtain dialkyl carbonate mixture containing carbon atoms no more than 5, dialkyl carbonate mixture containing carbon atoms of 6 to 9 and dialkyl carbonate mixture containing carbon atoms of 10 to 17 respectively according to Embodiment 2, then mixing the dialkyl carbonate mixtures according to the composition and the volume percentage in Table 1 to obtain the blended gasoline 8-3 and 8-4.

The quality results of the blended gasoline produced by the invention refer to Table 2.

TABLE 1

Component and volume percentage of the blended gasoline

| Embodiment | Ethyl methyl carbonate (%) | Diethyl carbonate (%) | Dipropyl carbonate (%) | Dibutyl carbonate (%) |
|---|---|---|---|---|
| 8-1 | 10 | 50 | 20 | 20 |
| 8-2 | 5 | 80 | 15 | 0 |

| Embodiment | Dialkyl carbonate mixture containing no more than 5 carbon atoms | Dialkyl carbonate mixture containing 6 to 9 carbon atoms |
|---|---|---|
| 8-3 | 80 | 20 |
| 8-4 | 90 | 10 |

TABLE 2

Quality results of the blended gasoline

| Item | | GB/T 17930-2006 | Embodiment 8-1 | Embodiment 8-2 | Embodiment 8-3 | Embodiment 8-4 | Testing method |
|---|---|---|---|---|---|---|---|
| Calorific value MJ/kg | | — | 42.6 | 43.8 | 42.2 | 41.9 | GB-T384 |
| Research octane number (RON) | | ≥93 | 97.8 | 97.2 | 97.0 | 97.5 | GB/T5487 |
| Antiknock index (RON + MON)/2 | | ≥88 | 91.4 | 91.6 | 91.0 | 90.8 | GB/T 503 |
| Lead content g/L | | ≤0.005 | <0.0025 | <0.0025 | <0.0025 | <0.0025 | GB/T 8020 |
| Boiling range | 10% evaporating temperature ° C. | ≤70 | 56.5 | 58.6 | 57.8 | 55.2 | GB/T 6536 |
| | 50% evaporating temperature ° C. | ≤120 | 78.1 | 80.5 | 79.6 | 76.3 | |

TABLE 2-continued

Quality results of the blended gasoline

| Item | GB/T 17930-2006 | Embodiment 8-1 | Embodiment 8-2 | Embodiment 8-3 | Embodiment 8-4 | Testing method |
|---|---|---|---|---|---|---|
| 90% evaporating temperature ° C. | ≤190 | 158.6 | 160.8 | 160.0 | 156.4 | |
| Final boiling point ° C. | ≤205 | 188.1 | 190.2 | 188.6 | 185.9 | |
| Residue (volume percentage)% | ≤2 | 1 | 1 | 1 | 1 | |
| Vapor pressure (KPa) From Nov.1 to Apr.30 | ≤88 | 56 | 58 | 57 | 55 | GB/T 8017 |
| solvent washed gum content mg/100 mL | ≤5 | 0.5 | 0.6 | 0.5 | 0.4 | GB/T 8019 |
| Inducing period/min | ≥480 | >480 | >480 | >480 | >480 | GB/T 8018 |
| Sulphur content, mass percentage % | ≤0.05 | 0.0032 | 0.0036 | 0.0030 | 0.0028 | SH/T 0689 |
| Mercaptan (satisfying one of the following demands): | | | | | | |
| Doctor test | passed | passed | passed | passed | passed | SH/T 0174 |
| Sulphur content of mercaptan, mass percentage % | ≤0.001 | <0.001 | <0.001 | <0.001 | <0.001 | GB/T 1792 |
| Copper sheet corrosion (50° C., 3 h) grade | 1 | 1a | 1a | 1a | 1a | GB/T 5096 |
| Water-soluble acid or alkali | No | No | No | No | No | GB/T 259 |
| Mechanical impurities | No | No | No | No | No | visual inspection |
| Water mass percentage % | ≤0.2 | 0.18 | 0.15 | 0.16 | 0.12 | SH/T 0246 |
| Other organic oxidizing compound mass percentage % | ≤0.5 | 0.42 | 0.45 | 0.40 | 0.43 | SH/T 0663 |
| Manganese content g/L | ≤0.016 | <0.0020 | <0.0020 | <0.0020 | <0.0020 | SH/T 0711 |
| Iron content g/L | ≤0.01 | <0.0010 | <0.0010 | <0.0010 | <0.0010 | SH/T 0712 |

Embodiment 9

Producing the Blended Diesel Oil

Producing dialkyl carbonates containing volume percentage not less than 95% respectively according to Embodiment 1 (or directly adopting normal commercial dialkyl carbonates), then mixing the dialkyl carbonates according to the composition and the volume percentage in Table 3 to obtain the blended diesel oil 9-1 and 9-2.

Performing a mixed ester exchange reaction between dimethyl carbonate (or ethylene carbonate) and the mixture which containing ethanol, n-propyl alcohol, n-butyl alcohol, n-amyl alcohol and n-hexyl carbonate to obtain dialkyl carbonate mixture containing carbon atoms no more than 5, dialkyl carbonate mixture containing carbon atoms of 6 to 9 and dialkyl carbonate mixture containing carbon atoms of 10 to 17 respectively according to Embodiment 2, then mixing the dialkyl carbonate mixtures according to the composition and the volume percentage in Table 3 to obtain the blended diesel oil 9-3 and 9-4.

The quality results of the blended diesel oil produced by the invention refer to Table 4.

TABLE 3

Component and volume percentage of the blended diesel oil

| Embodiment | Ethyl methyl carbonate (%) | Diethyl carbonate (%) | Dipropyl carbonate (%) | Dibutyl carbonate (%) | Diamyl carbonate (%) | Dihexyl carbonate (%) |
|---|---|---|---|---|---|---|
| 9-1 | 0 | 10 | 30 | 30 | 30 | 0 |
| 9-2 | 5 | 15 | 0 | 60 | 10 | 10 |

| Embodiment | Dialkyl carbonate mixture containing no more than 5 carbon atoms | Dialkyl carbonate mixture containing carbon atoms of 6 to 9 | Dialkyl carbonate mixture containing carbon atoms of 10 to 13 |
|---|---|---|---|
| 9-3 | 20 | 50 | 30 |
| 9-4 | 15 | 60 | 25 |

TABLE 4

Quality results of the blended diesel oil

| Item | GB/T 19147-2003 | Embodiment 9-1 | Embodiment 9-2 | Embodiment 9-3 | Embodiment 9-4 | Testing method |
|---|---|---|---|---|---|---|
| Calorific value MJ/kg | — | 40.2 | 40.9 | 39.6 | 41.3 | GB-T384 |
| Oxidation stability mg/mL | ≤2.5 | 2.4 | 2.3 | 2.4 | 2.2 | SH/T 0175 |
| Sulphur content mass percentage % | ≤0.15 | 0.0325 | 0.0512 | 0.0438 | 0.0386 | GB/T 380 |
| Acid value (mg/g) | ≤0.09 | 0.064 | 0.068 | 0.060 | 0.062 | GB/T 7304 |
| 10% residual carbon in distillation % | ≤0.3 | 0.02 | 0.03 | 0.02 | 0.03 | GB/T17144 |
| Ash mass percentage % | ≤0.01 | 0.002 | 0.002 | 0.004 | 0.003 | GB/T 508 |
| Copper sheet corrosion (50° C., 3 h) grade | 1 | 1a | 1a | 1a | 1a | GB/T 5096 |
| Water mass percentage %* | ≤0.035 | 0.016 | 0.020 | 0.018 | 0.015 | SH/T 0246 |
| Mechanical impurities | No | No | No | No | No | GB/T 511 |
| Kinematic viscosity 20° C. | 3.0-8.0 | 3.419 | 3.682 | 3.873 | 3.541 | GB/T 265 |
| Flash point (closed) ° C. | ≥55 | 77.5 | 77.8 | 77.6 | 78.3 | GB/T 261 |
| Cold filter plugging point ° C. | ≤12 | −34 | −32 | −35 | −36 | SH/T 0248 |
| Condensation point ° C. | ≤10 | −49 | −50 | −52 | −48 | GB/T 510 |
| Cetane number | ≥45 | 53 | 55 | 58 | 52 | GB/T 386 |
| Density 20° C. g/cm$^3$ | 820-860 | 842.7 | 833.3 | 856.8 | 849.5 | GB.T 1884 |
| Boiling range 50% recovery temperature ° C. | ≤300 | 250.9 | 248.6 | 255.2 | 258.3 | GB/T6536-2010 |
| 90% recovery temperature ° C. | ≤355 | 281.9 | 290.6 | 287.4 | 280.5 | |
| 95% recovery temperature ° C. | ≤365 | 290.2 | 298.4 | 295.2 | 292.1 | |

Embodiment 10

Producing the Blended Kerosene

Producing dialkyl carbonates with volume percentage not less than 95% respectively according to Embodiment 1 (or directly adopting normal commercial dialkyl carbonates), then mixing the dialkyl carbonates according to the composition and the volume percentage in Table 5 to obtain the blended kerosene 10-1 and 10-2.

Performing a mixed ester exchange reaction between dimethyl carbonate (or ethylene carbonate) and the mixture which containing ethanol, n-propyl alcohol, n-butyl alcohol and high carbon alcohols which containing carbon atoms of 5 to 8 to obtain dialkyl carbonate mixture containing carbon atoms no more than 5, dialkyl carbonate mixture containing carbon atoms of 6 to 9 and dialkyl carbonate mixture containing carbon atoms of 10 to 17 respectively according to Embodiment 2, then mixing the dialkyl carbonate mixtures according to the composition and the volume percentage in Table 5 to obtain the blended kerosene 10-3 and 10-4.

The quality results of the blended kerosene produced by the invention refer to Table 6.

TABLE 5

Component and volume percentage of the blended kerosene

| Embodiment | Ethyl methyl carbonate (%) | Diethyl carbonate (%) | Dipropyl carbonate (%) | Dibutyl carbonate (%) | Diamyl carbonate (%) | Dihexyl carbonate (%) | Diheptyl carbonate (%) | Dioctyl carbonate (%) |
|---|---|---|---|---|---|---|---|---|
| 10-1 | 5 | 20 | 0 | 60 | 0 | 0 | 15 | 0 |
| 10-2 | 10 | 30 | 10 | 30 | 10 | 10 | 0 | 0 |

| Embodiment | Dialkyl carbonate mixture containing no more than 5 carbon atoms (%) | Dialkyl carbonate mixture containing 6 to 9 carbon atoms (%) | Dialkyl carbonate mixture containing 10 to 17 carbon atoms (%) |
|---|---|---|---|
| 10-3 | 35 | 50 | 15 |
| 10-4 | 20 | 60 | 20 |

TABLE 6

Quality results of the blended kerosene

| Item | ASTM D190 | Embodiment 10-1 | Embodiment 10-2 | Embodiment 10-3 | Embodiment 10-4 | Testing method |
|---|---|---|---|---|---|---|
| Calorific value MJ/kg | ≥43.5 | 49.3 | 50.6 | 51.8 | 49.8 | D 4529 |
| Cetane number | ≥80.7 | 90 | 92 | 91 | 88 | D2700 |
| Density g/cm$^3$ | report | 0.825 | 0.835 | 0.830 | 0.828 | D 1298 |
| Sulphur content % | ≤0.05 | 0.02 | 0.03 | 0.02 | 0.02 | D 1266 |
| Flash point (closed) ° C. | ≥55 | 80 | 81 | 80 | 82 | GB/T261 |
| Condensation point ° C. | ≤−58 | −75 | −72 | −74 | −76 | D 2386 |
| Oxidation stability (110° C.) h | ≥25 | 30 | 32 | 28 | 31 | EN14112 |
| Copper sheet corrosion (50° C., 3 h) grade | 1 | 1 | 1 | 1 | 1 | D 130 |

Embodiment 11

Producing the Liquid Fuel Used as the Blended Gasoline from 1,4-Pentanediol Carbonate and Mixed Alcohol Adding 1,4-pentanediol carbonate prepared by the embodiment 3 and mixed alcohol containing methanol and ethanol in a tubular ester exchange reactor; then adding the metal-rare earth oxide composite catalyst prepared by the embodiment 3, in the reactor an ester exchange reaction is performed to obtain a mixture of dialkyl carbonates containing carbon atoms of 3 to 5, wherein the mole ratio between 1,4-pentanediol carbonate, methanol and ethanol is 1:2:2; the weight ratio of the metal-rare earth oxide composite catalyst to the total weight of 1,4-pentanediol carbonate and mixed alcohol is 1:100; the ester exchange reaction is performed at a temperature of 150° C. and under an absolute pressure of 2 MPa for 30 min to obtain a mixture of dialkyl carbonates.

Distilling the prepared mixture of dialkyl carbonates under a pressure of 0.01 MPa and at a temperature of 200° C., and collecting fraction of 80° C. to 90° C. to obtain the liquid fuel (namely dialkyl carbonate mixture with carbon atoms no more than 5, and its volume percentage in the liquid fuel is 100%); the liquid fuel can be used as blended gasoline; and its quality results refer to Table 7.

Embodiment 12

Producing the Liquid Fuel Used as the Blended Gasoline from 1,4-Pentanediol Carbonate and Mixed Alcohol Adding 1,4-pentanediol carbonate prepared by the embodiment 3 and mixed alcohol containing ethanol, normal propyl alcohol and n-butyl alcohol in a tubular ester exchange reactor; then adding the metal-rare earth oxide composite catalyst prepared by the embodiment 3, in the reactor an ester exchange reaction is performed to obtain a mixture of dialkyl carbonates containing carbon atoms of 5 to 9, wherein the mole ratio between 1,4-pentanediol carbonate, ethanol, normal propyl alcohol and n-butyl alcohol is 6:10:1:1; the weight ratio of the metal-rare earth oxide composite catalyst to the total weight of 1,4-pentanediol carbonate and mixed alcohol is 0.5:100; the ester exchange reaction is performed at a temperature of 160° C. and under an absolute pressure of 3 MPa for 30 minutes to obtain a mixture of dialkyl carbonates.

Distilling the prepared mixture of dialkyl carbonates under a pressure of 0.01 MPa and at a temperature of 200° C.; collecting fraction of 80° C. to 90° C. to obtain dialkyl carbonate mixture containing carbon atoms no more than 5; collecting fraction of 125° C. to 135° C. to obtain dialkyl carbonate mixture containing carbon atoms of 6 to 9, and combing the fraction of 80° C. to 90° C. and the fraction of 125° C. to 135° C. to obtain the liquid fuel; the total volume percentage of the dialkyl carbonates containing no more than 5 carbon atoms in the liquid fuel is 67%, and the total volume percentage of the dialkyl carbonates containing carbon atoms of 6 to 9 in the liquid fuel is 33%; the liquid fuel can be used as blended gasoline; and its quality results refer to Table 7.

Embodiment 13

Producing the Liquid Fuel Used as the Blended Gasoline from 1,4-Pentanediol Carbonate and Mixed Alcohol Adding 1,4-pentanediol carbonate prepared by the embodiment 5 and mixed alcohol containing ethanol, cyclopropanol and isobutanol in a tubular ester exchange reactor; then adding the metal-rare earth oxide composite catalyst prepared by the embodiment 5, in the reactor an ester exchange reaction is performed to obtain a mixture of dialkyl carbonates containing carbon atoms of 5 to 9, wherein the mole ratio between 1,4-pentanediol carbonate, ethanol, cyclopropanol and isobutanol is 9:18:1:1; the weight ratio of the metal-rare earth oxide composite catalyst to the total weight of 1,4-pentanediol carbonate and mixed alcohol is 0.5:100; the ester exchange reaction is performed at a temperature of 160° C. and under an absolute pressure of 3 MPa for 30 minutes to obtain a mixture of dialkyl carbonates.

Distilling the prepared mixture of dialkyl carbonates under a pressure of 0.01 MPa and at a temperature of 200° C.; collecting fraction of 80° C. to 90° C. and fraction of 125° C. to 135° C. to obtain the liquid fuel; the total volume percentage of the dialkyl carbonates containing no more than 5 carbon atoms in the liquid fuel is 80%, and the total volume percentage of the dialkyl carbonates containing carbon atoms of 6 to 9 is 20%; the liquid fuel can be used as blended gasoline; and its quality results refer to Table 7.

Embodiment 14

Producing the Liquid Fuel Used as the Blended Diesel Oil from 1,4-Pentanediol Carbonate and Mixed Alcohol

Adding 1,4-pentanediol carbonate prepared by the embodiment 3 and mixed alcohol containing ethanol, normal propyl alcohol and n-amyl alcohol in a tubular ester exchange reactor; then adding the metal-rare earth oxide composite catalyst prepared by the embodiment 3, in the reactor an ester exchange reaction is performed to obtain a mixture of dialkyl carbonates containing carbon atoms of 5 to 11, wherein the mole ratio between 1,4-pentanediol carbonate, ethanol, normal propyl alcohol and n-amyl alcohol is 5:10:3:1; the weight ratio of the metal-rare earth oxide composite catalyst to the total weight of the 1,4-pentanediol carbonate and mixed alcohol is 1:100; the ester exchange reaction is performed at a temperature of 155° C. and under an absolute pressure of 2.5 MPa for 40 minutes to obtain a mixture of dialkyl carbonates.

Distilling the prepared mixture of dialkyl carbonates under a pressure of 0.01 MPa and at a temperature of 200° C.; collecting fraction of 80° C. to 90° C. to obtain a mixture of dialkyl carbonates containing carbon atoms no more than 5; collecting fraction of 125° C. to 135° C. to obtain a mixture of dialkyl carbonates containing carbon atoms of 6 to 9; collecting fraction of 180° C. to 200° C. to obtain a mixture of dialkyl carbonates containing carbon atoms of 10 to 17; and combing fractions of 80° C. to 90° C., 125° C. to 135° C. and 180° C. to 200° C. to obtain the liquid fuel; the total volume percentage of the dialkyl carbonates containing no more than 5 carbon atoms in the liquid fuel is 20%, the total volume percentage of the dialkyl carbonates containing carbon atoms of 6 to 9 is 60%, and the total volume percentage of the dialkyl carbonates containing carbon atoms of 10 to 17 is 20%; the liquid fuel can be used as blended diesel oil; and its quality results refer to Table 8.

Embodiment 15

Producing the Liquid Fuel Used as the Blended Diesel Oil from 1,4-Pentanediol Carbonate and Mixed Alcohol

Adding 1,4-pentanediol carbonate prepared by the embodiment 3 and mixed alcohol containing ethanol, isopropyl alcohol and furfuryl alcohol in a tubular ester exchange reactor; then adding the metal-rare earth oxide composite catalyst prepared by the embodiment 3, in the reactor an ester exchange reaction is performed to obtain a mixture of dialkyl carbonates containing carbon atoms of 5 to 11, wherein the mole ratio between 1,4-pentanediol carbonate, ethanol, isopropyl alcohol and furfuryl alcohol is 10:20:5:3; the weight ratio of the metal-rare earth oxide composite catalyst to the total weight of the 1,4-pentanediol carbonate and mixed alcohol is 0.2:100; the ester exchange reaction is performed at a temperature of 180° C. and under an absolute pressure of 4 MPa for 15 minutes to obtain a mixture of dialkyl carbonates.

Distilling the prepared mixture of dialkyl carbonates under a pressure of 0.01 MPa and at a temperature of 200° C.; collecting fractions of 80° C. to 90° C., 125° C. to 135° C. and 180° C. to 200° C. to obtain the liquid fuel; the total volume percentage of the dialkyl carbonates containing no more than 5 carbon atoms in the liquid fuel is 20%, the total volume percentage of the dialkyl carbonates containing carbon atoms of 6 to 9 is 50% and the total volume percentage of the dialkyl carbonates containing carbon atoms of 10 to 17 is 30%; the liquid fuel can be used as blended gasoline; and its quality results refer to Table 8.

Embodiment 16

Producing the Liquid Fuel Used as the Blended Diesel Oil from 1,4-Pentanediol Carbonate and Mixed Alcohol

Adding 1,4-pentanediol carbonate prepared by the embodiment 6 and mixed alcohol containing ethanol, isobutyl alcohol, n-octyl alcohol and furfuryl alcohol in a tubular ester exchange reactor; then adding the metal-rare earth oxide composite catalyst prepared by the embodiment 6, in the reactor an ester exchange reaction is performed to obtain a mixture of dialkyl carbonates containing carbon atoms of 5 to 17, wherein the mole ratio between 1,4-pentanediol carbonate, ethanol, isobutyl alcohol, n-octyl alcohol and furfuryl alcohol is 10:18:6:1.5:1.5; the weight ratio of the metal-rare earth oxide composite catalyst to the total weight of 1,4-pentanediol carbonate and mixed alcohol is 0.8:100; the ester exchange reaction is performed at a temperature of 160° C. and under an absolute pressure of 3 MPa for 30 minutes to obtain a mixture of dialkyl carbonates.

Distilling the prepared mixture of dialkyl carbonates under a pressure of 0.01 MPa and at a temperature of 200° C.; collecting fractions of 80° C. to 90° C., 125° C. to 135° C. and 180° C. to 200° C. to obtain the liquid fuel; the total volume percentage of the dialkyl carbonates containing no more than 5 carbon atoms in the liquid fuel is 10%, the total volume percentage of the dialkyl carbonates containing carbon atoms of 6 to 9 is 60% and the total volume percentage of the dialkyl carbonates containing carbon atoms of 10 to 17 is 30%; the produced liquid fuel can be used as blended diesel oil; and its quality results refer to Table 8.

Embodiment 17

Producing the Liquid Fuel Used as the Blended Kerosene from 1,4-Pentanediol Carbonate and Mixed Alcohol

Adding 1,4-pentanediol carbonate prepared by the embodiment 3 and mixed alcohol containing ethanol, cyclobutyl alcohol and n-hexanol in a tubular ester exchange reactor; then adding the metal-rare earth oxide composite catalyst prepared by the embodiment 3, in the reactor an ester exchange reaction is performed to obtain a mixture of dialkyl carbonates containing carbon atoms of 5 to 13, wherein the mole ratio between 1,4-pentanediol carbonate, ethanol, cyclobutyl alcohol and n-hexanol is 5:15:2:1; the weight ratio of the metal-rare earth oxide composite catalyst to the total weight of the 1,4-pentanediol carbonate and mixed alcohol is 0.2:100; the ester exchange reaction is performed at a temperature 150° C. and under an absolute pressure of 3 MPa for 20 minutes to obtain a mixture of dialkyl carbonates.

Distilling the prepared mixture of dialkyl carbonates under a pressure of 0.01 MPa and at a temperature of 200° C.; collecting fractions of 80° C. to 90° C., 125° C. to 135° C. and 180° C. to 200° C. to obtain the liquid fuel; the total volume percentage of the dialkyl carbonates containing no more than 5 carbon atoms in the liquid fuel is 40%, the total volume percentage of the dialkyl carbonates containing carbon atoms of 6 to 9 is 40% and the total volume percentage of the dialkyl carbonates containing carbon atoms of 10 to 17 is 20%; the produced liquid fuel can be used as blended kerosene; and its quality results refer to Table 9.

Embodiment 18

Producing the Liquid Fuel Used as the Blended Kerosene from 1,4-Pentanediol Carbonate and Mixed Alcohol 5

Adding 1,4-pentanediol carbonate prepared by the embodiment 5 and mixed alcohol containing ethanol, n-propyl alcohol, isoamyl alcohol and furfuryl alcohol in a tubular ester exchange reactor; and then adding the metal-rare earth oxide composite catalyst prepared by the embodiment 5, in the reactor an ester exchange reaction is performed to obtain a mixture of dialkyl carbonates containing carbon atoms of 5 to 11, wherein the mole ratio between 1,4-pentanediol carbonate, ethanol, n-propyl alcohol, isoamyl alcohol and furfuryl alcohol is 10:20:6:1:1; the weight ratio of the metal-rare earth oxide composite catalyst to the total weight of 1,4-pentanediol carbonate and mixed alcohol is 0.5:100; the ester exchange reaction is performed at a temperature of 160° C. and under an absolute pressure of 3 MPa for 30 minutes to obtain a mixture of dialkyl carbonates.

Distilling the prepared mixture of dialkyl carbonates under a pressure of 0.01 MPa and at a temperature of 200° C.; collecting fractions of 80° C. to 90° C., 125° C. to 135° C. and 180° C. to 200° C. to obtain the liquid fuel; the total volume percentage of the dialkyl carbonates containing no more than 5 carbon atoms in the liquid fuel is 20%, the total volume percentage of the dialkyl carbonates containing carbon atoms of 6 to 9 is 60% and the total volume percentage of the dialkyl carbonates containing carbon atoms of 10 to 17 is 20%; the produced liquid fuel can be used as blended kerosene; and its quality results refer to Table 9.

Embodiment 19

Producing the Liquid Fuel Used as the Blended Kerosene From 1,4-Pentanediol Carbonate and Mixed Alcohol Adding 1,4-pentanediol carbonate prepared by the embodiment 3 and mixed alcohol containing ethanol, cyclopropyl alcohol, isooctyl alcohol and furfuryl alcohol in a tubular ester exchange reactor, and then adding the metal-rare earth oxide composite catalyst prepared by the embodiment 3, in the reactor an ester exchange reaction is performed to obtain a mixture of dialkyl carbonates containing carbon atoms of 5 to 17, wherein the mole ratio between 1,4-pentanediol carbonate, ethanol, cyclopropyl alcohol, isooctyl alcohol and furfuryl alcohol is 10:18:5:1:1; the weight ratio of the metal-rare earth oxide composite catalyst to the total weight of 1,4-pentanediol carbonate and mixed alcohol is 1:100; the ester exchange reaction is performed at a temperature of 160° C. and under an absolute pressure of 3 MPa for 30 minutes to obtain the mixture of dialkyl carbonates.

Distilling the prepared mixture of dialkyl carbonates under a pressure of 0.01 MPa and at a temperature of 200° C.; collecting fractions of 80° C. to 90° C., 125° C. to 135° C. and 180° C. to 200° C. to obtain the liquid fuel; the total volume percentage of the dialkyl carbonates containing no more than 5 carbon atoms in the liquid fuel is 30%, the total volume percentage of the dialkyl carbonates containing carbon atoms of 6 to 9 is 50% and the total volume percentage of the dialkyl carbonate containing carbon atoms of 10 to 17 is 20%; the produced liquid fuel can be used as blended kerosene; and its quality results refer to Table 9.

TABLE 7

Quality results of the produced dialkyl carbonates used as blended gasoline

| Item | GB/T17930-2006 | Embodiment 11 | Embodiment 12 | Embodiment 13 | Testing method |
|---|---|---|---|---|---|
| Calorific value MJ/kg | — | 42.0 | 43.2 | 42.8 | GB-T384 |
| Research octane number (RON) | ≥93 | 97.0 | 97.4 | 97.6 | GB/T5487 |
| Antiknock index (RON + MON)/2 | ≥88 | 91.1 | 91.3 | 91.5 | GB/T 503 |
| Lead content g/L | ≤0.005 | <0.0025 | <0.0025 | <0.0025 | GB/T 8020 |
| Boiling range 10% evaporating temperature ° C. | <70 | 56.4 | 57.6 | 57.9 | GB/T 6536 |
| 50% evaporating temperature ° C. | ≤120 | 78.1 | 79.2 | 79.8 | |
| 90% evaporating temperature ° C. | ≤190 | 158.2 | 159.8 | 160.1 | |
| Final boiling point ° C. | ≤205 | 188.0 | 189.4 | 188.5 | |
| Residue (volume percentage) % | ≤2 | 1 | 1 | 1 | |
| Vapor pressure (KPa) From Nov. 1 to Apr. 30 | ≤88 | 56 | 57 | 57 | GB/T 8017 |
| solvent washed gum content mg/100 mL | ≤5 | 0.5 | 0.6 | 0.5 | GB/T 8019 |
| Inducing period/min | ≥480 | >480 | >480 | >480 | GB/T 8018 |
| Sulphur content, mass percentage % | ≤0.05 | 0.0031 | 0.0037 | 0.0032 | SH/T 0689 |
| Mercaptan (satisfying one of the following demands): | | | | | |
| Doctor test | passed | passed | passed | passed | SH/T 0174 |
| Sulphur content of mercaptan, mass percentage % | ≤0.001 | <0.001 | <0.001 | <0.001 | GB/T 1792 |
| Copper sheet corrosion (50° C., 3 h) grade | 1 | 1a | 1a | 1a | GB/T 5096 |
| Water-soluble acid or alkali | No | No | No | No | GB/T 259 |
| Mechanical impurities | No | No | No | No | visual inspection |

TABLE 7-continued

Quality results of the produced dialkyl carbonates used as blended gasoline

| Item | GB/T17930-2006 | Embodiment 11 | Embodiment 12 | Embodiment 13 | Testing method |
|---|---|---|---|---|---|
| Water mass percentage % | ≤0.2 | 0.16 | 0.18 | 0.19 | SH/T 0246 |
| Other organic oxidizing compound mass percentage % | ≤0.5 | 0.40 | 0.42 | 0.44 | SH/T 0663 |
| Manganese content g/L | ≤0.016 | <0.0020 | <0.0020 | <0.0020 | SH/T 0711 |
| Iron content g/L | ≤0.01 | <0.0010 | <0.0010 | <0.0010 | SH/T 0712 |

TABLE 8

Quality results of the produced dialkyl carbonates used as blended diesel oil

| Item | GB/T 19147-2003 | Embodiment 14 | Embodiment 15 | Embodiment 16 | Testing method |
|---|---|---|---|---|---|
| Calorific value MJ/kg | — | 41.3 | 40.3 | 42.1 | GB-T384 |
| Oxidation stability mg/mL | ≤2.5 | 2.1 | 2.3 | 2.2 | SH/T 0175 |
| Sulphur content mass percentage % | ≤0.15 | 0.0376 | 0.0508 | 0.0419 | GB/T 380 |
| Acid value (mg/g) | ≤0.09 | 0.068 | 0.065 | 0.062 | GB/T 7304 |
| 10% residual carbon in distillation % | ≤0.3 | 0.03 | 0.03 | 0.02 | GB/T17144 |
| Ash mass percentage % | ≤0.01 | 0.003 | 0.002 | 0.004 | GB/T 508 |
| Copper sheet corrosion (50° C., 3 h) grade | 1 | 1a | 1a | 1a | GB/T 5096 |
| Water mass percentage %* | ≤0.035 | 0.017 | 0.020 | 0.019 | SH/T 0246 |
| Mechanical impurities | No | No | No | No | GB/T 511 |
| Kinematic viscosity 20° C. | 3.0-8.0 | 3.456 | 3.679 | 3.868 | GB/T 265 |
| Flash point (closed) ° C. | ≥55 | 77.4 | 77.7 | 77.9 | GB/T 261 |
| Cold filter plugging point ° C. | ≤12 | −33 | −34 | −32 | SH/T 0248 |
| Condensation point ° C. | ≤−10 | −55 | −54 | −48 | GB/T 510 |
| Cetane number | ≥45 | 61 | 66 | 72 | GB/T 386 |
| Density 20° C. g/cm³ | 820-860 | 841.9 | 832.3 | 856.0 | GB.T 1884 |
| Boiling range 50% recovery temperature ° C. | ≤300 | 252.9 | 249.8 | 256.2 | GB/T6536-2010 |
| Boiling range 90% recovery temperature ° C. | ≤355 | 285.6 | 290.0 | 288.0 | |
| Boiling range 95% recovery temperature ° C. | ≤365 | 291.4 | 297.6 | 294.3 | |

TABLE 9

Quality results of the produced dialkyl carbonates used as blended kerosene

| Item | ASTM D190 | Embodiment 17 | Embodiment 18 | Embodiment 19 | Testing method |
|---|---|---|---|---|---|
| Calorific value MJ/kg | ≥43.5 | 45.8 | 46.5 | 46.9 | D 4529 |
| Cetane number | ≥80.7 | 91 | 91 | 92 | D2700 |
| Density g/cm³ | report | 0.828 | 0.832 | 0.835 | D 1298 |
| Sulphur content % | ≤0.05 | 0.02 | 0.03 | 0.02 | D 1266 |
| Flash point (closed) ° C. | ≥55 | 81 | 81 | 80 | GB/T261 |
| Condensation point ° C. | ≤−58 | −76 | −73 | −71 | D 2386 |
| Oxidation stability (110° C.) h | ≥25 | 28 | 32 | 31 | EN14112 |
| Copper sheet corrosion (50° C., 3 h) grade | 1 | 1 | 1 | 1 | D 130 |

We can know from the previous results that:

1. The blended gasoline, diesel oil and kerosene produced by the present invention are similar to the normal gasoline, diesel oil and kerosene in burning calorific value, and various quality indexes of them are accordant with regulations of related national standards; they could be used as the gasoline, diesel oil, kerosene or components thereof for replacing the existing petroleum liquid fuel, biological liquid fuel and other fuels.

2. Various liquid fuels produced by the present invention are free from toxicity, clean to burn, good in lubrication and oxidation stability and are environmental-friendly; the liquid fuels are capable of effectively inhibiting corrosion and abrasion of equipment, so as to prolong service lives of engine and metal parts.

The invention claimed is:

1. A process for the production of liquid fuel, wherein the process comprises performing an ester exchange reaction between a cyclic carbonate and a monohydric alcohol selected from one or more of the group consisting of C1-C8 linear chain alcohol, C3-C8 branched chain alcohol, C3-C8 cyclic alcohol and alcohol containing furan ring,
  wherein the cyclic carbonate is 1,4-pentanediol carbonate, and wherein the process further comprises performing a cycloaddition reaction between 2-methyl tetrahydrofuran and carbon dioxide to produce the 1,4-pentanediol carbonate.

2. The process for the production of the liquid fuel according to claim 1, wherein the cycloaddition reaction is performed in the presence of magnesium-zinc-rare earth oxide composite catalyst; the magnesium-zinc-rare earth oxide composite catalyst includes magnesium oxide, zinc oxide and rare earth oxide; the mole ratio of magnesium oxide to zinc oxide is 1:1 to 4:1; and the mass percentage of the rare earth oxide in the magnesium-zinc-rare earth oxide composite catalyst is in the range of 0.1% to 1%.

3. The process for the production of the liquid fuel according to claim 1, wherein the mole ratio of 2-methyl tetrahydrofuran to carbon dioxide in the cycloaddition reaction is 1:1 to 1:20; and the weight ratio of the magnesium-zinc-rare earth oxide composite catalyst to 2-methyl tetrahydrofuran is 0.1:100 to 5:100.

4. The process for the production of the liquid fuel according to claim 1, wherein the cycloaddition reaction is performed at a temperature in the range of 80° C. to 150° C. and under an absolute pressure in the range of 2 MPa to 10 MPa for 5 minutes to 120 minutes.

5. The process for the production of the liquid fuel according to claim 1, wherein the ester exchange reaction is performed in the presence of catalyst, the catalyst is selected from the group consisting of alkaline catalyst and metal-earth oxide composite catalyst.

6. The process for the production of the liquid fuel according to claim 5, wherein the weight ratio of the catalyst to the carbonate is in the range of 0.1:100 to 5:100, the mole ratio of the carbonate to the monohydric alcohol is in the range of 1:1 to 1:20, and the ester exchange reaction is performed at a temperature in the range of 60° C. to 300° C. and under an absolute pressure in the range of 0.1 MPa to 8 MPa for 5 minutes to 300 minutes.

7. The process for the production of the liquid fuel according to claim 5, wherein the alkaline catalyst is selected from the group consisting of alkali metal carbonate, alkali metal organic salt and solid alkaline catalyst.

8. The process for the production of the liquid fuel according to claim 5, wherein the metal-earth oxide composite catalyst includes metallic oxide and rare earth oxide, wherein the weight ratio of the metallic oxide to the rare earth oxide is (90-99):(1-10).

9. The process for the production of the liquid fuel according to claim 8, wherein the metallic oxide is selected from one or more of the group consisting of zinc oxide, aluminum oxide and stannous oxide; and the rare earth oxide is selected from one or more of the group consisting of lanthanum oxide and cerium oxide.

10. The process for the production of the liquid fuel according to claim 1, wherein the liquid fuel is dialkyl carbonates with the structural formula of

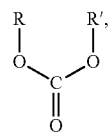

wherein R and R' are same or different, and R and R' are selected from the group consisting of C1-C8 linear chain alkyl, C3-C8 branched chain alkyl, C3-C8 naphthene base and alkyl containing furan ring.

11. The process for the production of the liquid fuel according to claim 10, wherein the C1-C8 linear chain alkyl is selected from the group consisting of ethyl, propyl, butyl, amyl and octyl, the C3-C8 branched chain alkyl is selected from the group consisting of isopropyl and isobutyl, the C3-C8 naphthene base is selected from the group consisting of cyclopropyl and cyclobutyl, the alkyl containing furan ring is furfuryl alcohol base.

12. The process for the production of the liquid fuel according to claim 10, wherein total volume percentage of dialkyl carbonates containing carbon atoms no more than 5 in the liquid fuel is in the range of 60% to 100%, and total volume percentage of dialkyl carbonates containing carbon atoms of 6 to 9 in the liquid fuel is in the range of 0 to 40%.

13. The process for the production of the liquid fuel according to claim 12, wherein the liquid fuel is used as gasoline or gasoline component.

14. The process for the production of the liquid fuel according to claim 10, wherein total volume percentage of dialkyl carbonates containing carbon atoms no more than 5 in the liquid fuel is in the range of 10% to 20%, total volume percentage of dialkyl carbonates containing carbon atoms of 6 to 9 in the liquid fuel is in the range of 40% to 60%, and total volume percentage of dialkyl carbonates containing carbon atoms of 10 to 17 in the liquid fuel is in the range of 20% to 30%.

15. The process for the production of the liquid fuel according to claim 14, wherein the liquid fuel is used as diesel oil or diesel oil component.

16. The process for the production of the liquid fuel according to claim 10, wherein total volume percentage of dialkyl carbonates containing carbon atoms no more than 5 in the liquid fuel is in the range of 20% to 40%, total volume percentage of dialkyl carbonates containing carbon atoms of 6 to 9 in the liquid fuel is in the range of 40% to 60%, and total volume percentage of dialkyl carbonates containing carbon atoms of 10 to 17 in the liquid fuel is in the range of 10% to 20%.

17. The process for the production of the liquid fuel according to claim 10, wherein the liquid fuel is used as kerosene or kerosene component.

* * * * *